(12) United States Patent
Chan et al.

(10) Patent No.: US 7,248,371 B2
(45) Date of Patent: Jul. 24, 2007

(54) OPTICAL IMAGE MEASURING APPARATUS

(75) Inventors: Kinpui Chan, Yamagata (JP);
Masahiro Akiba, Yamagata (JP);
Yasufumi Fukuma, Tokyo (JP);
Hiroyuki Otsuka, Tokyo (JP); Hisashi Tsukada, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 241 days.

(21) Appl. No.: 11/091,653

(22) Filed: Mar. 29, 2005

(65) Prior Publication Data

US 2005/0219545 A1 Oct. 6, 2005

(30) Foreign Application Priority Data

Mar. 30, 2004 (JP) ............................. 2004-100742

(51) Int. Cl.
*G01B 9/02* (2006.01)
(52) U.S. Cl. ...................................... 356/497; 356/489
(58) Field of Classification Search ................ 356/479, 356/497, 489, 485, 511
See application file for complete search history.

(56) References Cited

U.S. PATENT DOCUMENTS

| | | | |
|---|---|---|---|
| 5,465,147 A | 11/1995 | Swanson | |
| 2006/0028652 A1* | 2/2006 | Chan et al. | 356/497 |
| 2006/0055939 A1* | 3/2006 | Akiba et al. | 356/497 |
| 2006/0077395 A1* | 4/2006 | Chan et al. | 356/497 |
| 2006/0215172 A1* | 9/2006 | Abe | 356/497 |

FOREIGN PATENT DOCUMENTS

| | | |
|---|---|---|
| JP | 3245135 | 10/2001 |
| JP | 2001-330558 | 11/2001 |
| WO | 03/012405 | 2/2003 |

OTHER PUBLICATIONS

European Search Report in connection with European Patent Application No. 05006896, dated Jul. 26, 2005.
N. Tanno, "The imaging technic of the optical coherence tomography and its application to living organism image;" *KOGAKU (Japanese Journal of Optics)*; vol. 28, No. 3, pp. 116-125 (1999)./Discussed in the specification.

(Continued)

*Primary Examiner*—Hwa (Andrew) Lee
(74) *Attorney, Agent, or Firm*—Armstrong, Kratz, Quintos, Hanson & Brooks, LLP.

(57) ABSTRACT

Provided is an optical image measuring apparatus capable of easily changing a scanning interval of an object to be measured in a depth direction with high precision. The apparatus includes an interference optical system for superimposing signal light propagating through the object to be measured on reference light subjected to frequency shift to produce interference light, a reference mirror driving unit for driving a mirror to scan the object to be measured in the depth direction, shutters for sampling interference light beams, CCDs for storing charges for only a predetermined storage time and outputting electrical signals, a control unit for changing the storage time of the CCDs, a signal processing portion for calculating intensities and phases of interference light beams corresponding to each depth of the object to be measured which are successively detected by the CCDs during scanning based on the electrical signals successively outputted from the CCDs every changed storage time, and a setting operation unit for setting the storage time of the CCDs by an operator.

13 Claims, 3 Drawing Sheets

OTHER PUBLICATIONS

M. Akiba, et al. "Full-field optical coherence tomography by two-dimensional heterodyne detection with a pair of CCD cameras;" *Optics Letters*, vol. 28, No. 10, pp. 816-818, May 2003./Discussed in the specification.

K.P. Chan, et al. "Micrometre-resolution, optical imaging of objects through highly scattering media using a heterodyne detector array;" *Electronics Letters*, vol. 30, No. 21, pp. 1753-1754, Oct. 1994./Discussed in the specification.

Yoshizawa, et al. (editors), "Optical Heterodyne Technology;" the article by T. Nakajima, "Principle and application of the optical heterodyne method;" *New Technology Communications*, revised edition, 2003, pp. 1-11 and cover page (7 sheets total)./Discussed in the specification.

* cited by examiner

Interference Light Intensity

Interference Light Intensity

OPTICAL IMAGE MEASURING APPARATUS

BACKGROUND OF THE INVENTION

1. Field of the Invention

The present invention relates to an optical image measuring apparatus for applying a light beam to an object to be measured, particularly a light scattering medium and measuring a surface form or inner form of the object to be measured is measured based on a reflected light beam or a transmitted light beam to produce an image of a measured form. In particular, the present invention relates to an optical image measuring apparatus for measuring the surface form or inner form of the object to be measured by using an optical heterodyne detection method to produce the image of the measured form.

2. Description of the Related Art

In recent years, attention has been given to an optical image measuring technique for producing an image of a surface or inner portion of an object to be measured using a laser light source or the like. This optical image measuring technique is not hazardous to human bodies in contrast to a conventional X-ray CT. Therefore, the development of applications in the medical field has been particularly expected.

An example of a typical method in the optical image measuring technique is a low coherent interference method (also called an optical coherence tomography or the like). This method uses the low coherence of a broad band light source having a broad spectral width, such as a super luminescent diode (SLD). According to the method, reflection light from an object to be measured or light transmitted therethrough can be detected at superior distance resolution on the order of μm (for example, see Naohiro Tanno, "Kogaku" (Japanese Journal of Optics), Volume 28, No. 3, 116 (1999)).

FIG. 4 shows a basic structure of a conventional optical image measuring apparatus based on a Michelson interferometer, as an example of an apparatus using the low coherent interference method. An optical image measuring apparatus 100 includes a broad band light source 101, a mirror 102, a beam splitter 103, and a photo detector 104. An object to be measured 105 is made of a scattering medium. A light beam from the broad band light source 101 is divided by the beam splitter 103 into two, that is, reference light R propagating to the mirror 102 and signal light S propagating to the object to be measured 105. The reference light R is light reflected by the beam splitter 103. The signal light S is light transmitted through the beam splitter 103.

Here, as shown in FIG. 4, a propagating direction of the signal light S is set as a z-axis direction and a plane orthogonal to the propagating direction of the signal light S is defined as an x-y plane. The mirror 102 is shiftable in a direction indicated by a double-headed arrow in FIG. 4 (z-scanning direction).

The reference light R is subjected to Doppler frequency shift through z-scanning when reflected by the mirror 102. On the other hand, the signal light S is reflected on a surface of the object to be measured 105 and inner layers thereof when the object to be measured 105 is irradiated with the signal light S. The object to be measured 105 is made of the scattering medium, so reflection light of the signal light S may be a diffusing wave having random phases including multiple scattering. The signal light propagating through the object to be measured 105 and the reference light that propagates through the mirror 102 to be subjected to the frequency shift are superimposed on each other by the beam splitter 103 to produce interference light.

In the image measurement using such a low coherent interference method, a difference in optical path length between the signal light S and the reference light R is within a coherence length (coherent distance) on the order of μm of the light source. In addition, only a component of the signal light S which has phase correlation to the reference light R interferes with the reference light R. That is, only a coherent signal light component of the signal light S selectively interferes with the reference light R. Based on such fundamentals, the position of the mirror 102 is shifted by the z-scanning to change the optical path length of the reference light R, so that a light reflection profile of the inner layers of the object to be measured 105 is measured. The object to be measured 105 is also scanned with the irradiated signal light S in an x-y plane direction. The interference light is detected by the photo detector 104 during such scanning in the z-direction and the x-y plane direction. An electrical signal (heterodyne signal) outputted as a detection result is analyzed to obtain a two-dimensional sectional image of the object to be measured 105 (see Naohiro Tanno, "Kogaku" (Japanese Journal of Optics), Volume 28, No. 3, 116 (1999)).

Assume that an intensity of the reference light R and an intensity of the signal light S which are superimposed by the beam splitter 103 are given by $I_r$ and $I_s$, respectively, and a frequency difference between the reference light R and the signal light S and a phase difference therebetween are given by $f_{if}$ and $\Delta\theta$, respectively. In this case, a heterodyne signal as expressed by the following expression is outputted from the photo detector (for example, see Yoshizawa and Seta "Optical Heterodyne Technology (revised edition)", New Technology Communications (2003), p. 2).

Expression (1)

$$i(t) \propto I_r + I_s + 2\sqrt{I_r I_s} \cos(2\pi f_{if} t + \Delta\theta) \quad (1)$$

The third term of the right side of the expression (1) indicates an alternating current electrical signal and the frequency $f_{if}$ thereof is equal to a frequency of beat caused from the interference between the reference light R and the signal light S. The frequency $f_{if}$ of an alternating current component of the heterodyne signal is called a beat frequency or the like. The first and second terms of the right side of the expression (1) indicate direct current components of the heterodyne signal and correspond to a signal intensity of background light of interference light.

However, when the two-dimensional sectional image is obtained by the conventional low coherent interference method, it is necessary to scan the object to be measured 105 with a light beam and to successively detect reflection light waves from respective regions of the object to be measured 105 in a depth direction (z-direction) and a sectional direction (x-y plane direction). Therefore, the measurement of the object to be measured 105 requires a long time. In addition, it is hard to shorten a measurement time in view of measurement fundamentals.

In views of such problems, an optical image measuring apparatus for shortening a measurement time has been proposed. FIG. 5 shows a fundamental structure of an example of such an apparatus. As shown in FIG. 5, an optical image measuring apparatus 200 includes a broad band light source 201, a mirror 202, a beam splitter 203, a two-dimensional photo sensor array 204 serving as a photo detector, and lenses 206 and 207. A light beam emitted from the light source 201 is converted into a parallel light flux by the lenses 206 and 207 and a beam diameter thereof is widened thereby. Then, the parallel light flux is divided into two, that is, the reference light R and the signal light S by the beam splitter 203. The reference light R is subjected to Doppler frequency shift through z-scanning with the mirror 202. On the other hand, the signal light S is incident on the object to be measured 205 over a broad area of the x-y plane because the beam diameter is widened. Therefore, the signal light S becomes reflection light including information related to the surface and inner portion of the object to be measured 205 in the incident area. The reference light R and the signal light S are superimposed on each other by the beam splitter 203 and detected by elements (photo sensors) arranged in parallel on the two-dimensional photo sensor array 204. Thus, it is possible to obtain a two-dimensional sectional image of the object to be measured 205 in real time without light beam scanning.

An apparatus described in K. P. Chan, M. Yamada, and H. Inaba, "Electronics Letters", Vol. 30, 1753 (1994) has been known as such a non-scanning type optical image measuring apparatus. In the apparatus described in the same document, a plurality of heterodyne signals outputted from a two-dimensional photo sensor array are inputted to signal processing systems arranged in parallel to detect the amplitude and phase of each of the heterodyne signals.

However, when the spatial resolution of an image is improved, it is necessary to increase a number of elements of the array. In addition, it is necessary to prepare a signal processing system including a number of channels corresponding to the number of elements. Therefore, it is supposedly hard to actually use the apparatus in fields that require a high resolution image, such as a medical field and an industrial field.

Thus, the inventors of the present invention have proposed the following non-scanning type optical image measuring apparatus in JP 2001-330558 A (claims and specification paragraphs [0044] and [0072] to [0077]). The optical image measuring apparatus according to this proposal includes a light source for emitting a light beam, an interference optical system, and a signal processing portion. In the interference optical system, the light beam emitted from the light source is divided into two, that is, signal light propagating through an examined object arrangement position in which an object to be examined is arranged and reference light propagating on an optical path different from an optical path passing through the examined object arrangement position. The signal light propagating through the examined object arrangement position and the reference light propagating on the different optical path are superimposed on each other to produce interference light. The interference optical system includes a frequency shifter, light cutoff devices, and photo sensors. The frequency shifter shifts a frequency of the signal light and a frequency of the reference light relative to each other. In order to receive the interference light in the interference optical system, the interference light is divided into two parts. The light cutoff devices periodically cut off the two divided parts of the interference light to generate two interference light pulse trains with a phase difference of 90 degrees therebetween. The photo sensors respectively receive the two interference light pulse trains. The photo sensors each have a plurality of light receiving elements which are spatially arranged and separately obtain light receiving signals. The signal processing portion combines the plurality of light receiving signals obtained by the photo sensors to generate signals of the signal light which correspond to respective points of interest of a surface or inner layers of the object to be examined which is arranged in the examined object arrangement position on a propagating path of the signal light.

In the optical image measuring apparatus, the interference light in which the reference light and the signal light interfere with each other is divided into two parts. The two parts of the interference light are received by the two photo sensors (two-dimensional photo sensor arrays) and respectively sampled by the light cutoff devices (shutters) disposed in front of both sensor arrays. A phase difference of $\pi/2$ is set between sampling periods of the two divided parts of the interference light. Therefore, an intensity of the signal light and an intensity of the reference light which compose background light of the interference light and phase quadrature components (sine component and cosine component) of the interference light are detected. In addition, an intensity of the background light included in outputs from both the sensor arrays is subtracted from the outputs of both the sensor arrays to calculate two phase quadrature components of the interference light. An amplitude of the interference light is obtained based on the calculation result.

In addition, the inventors of the present invention have proposed the following optical image measuring apparatus in JP 3245135 B (claims and specification paragraphs [0072] to [0082]). The optical image measuring apparatus according to this proposal includes a light source for emitting a light beam and an interference optical system. In the interference optical system, the light beam emitted from the light source is divided into two, that is, signal light propagating through an examined object arrangement position in which an object to be examined is arranged and reference light propagating on an optical path different from an optical path passing through the examined object arrangement position. The signal light propagating through the examined object arrangement position and the reference light propagating on the different optical path are superimposed on each other to produce interference light in which the signal light and the reference light interfere with each other. The interference optical system includes a frequency shifter and an optical device. The frequency shifter shifts a frequency of the signal light and a frequency of the reference light relative to each other. The optical device is disposed on an optical path of at least one of the signal light and the reference light and periodically cuts off light. The cutoff frequency of the optical device is set to be equal to a frequency difference between the signal light and the reference light. According to the optical image measuring apparatus, the interference light can be sampled at the cutoff frequency equal to a beat frequency. Therefore, suitable optical heterodyne measurement is realized.

In the above-mentioned conventional optical image measuring apparatuses, the mirror (102 or 202) is shifted in the z-direction to scan the object to be measured in the depth direction, with the result that images at a plurality of depths are obtained. At this time, the mirror is shifted at predetermined speed. Therefore, the object to be measured is scanned in the depth direction at predetermined intervals. An image of the inner portion of the object is obtained at the depth set in, for example, 5 µm increments.

For example, when precise measurement is unnecessary, it is unnecessary to perform the scanning at small intervals. Therefore, scanning at larger intervals only needs to be performed. On the other hand, for example, when precise measurement is desired, it is necessary to perform scanning at smaller intervals.

To meet such needs, there is such a structure that a moving speed of the mirror is controlled to change a scanning interval. However, it is mechanistically hard to perform movement control of the mirror with high precision. Therefore, it is not easy to change a scanning interval of the object to be measured, that is, an interval for obtaining a sectional image of the object to be measured (image obtaining interval), with high precision.

SUMMARY OF THE INVENTION

The present invention has been made in view of the above-mentioned circumstances. An object of the present invention is to provide an optical image measuring apparatus capable of easily changing a scanning interval of an object to be measured in a depth direction thereof with high precision.

In order to achieve the above-mentioned object, a first aspect of the present invention provides an optical image measuring apparatus for obtaining an image of an object to be measured at a depth corresponding to a position of a reference object based on interference light, including: a light source for emitting a light beam; an interference optical system that divides the light beam emitted from the light source into signal light propagating through the object to be measured and reference light propagating through the reference object, shifts a frequency of the signal light and a frequency of the reference light relative to each other, and then superimposes the signal light propagating through the object to be measured and the reference light propagating through the reference object on each other to produce the interference light; intensity modulating means for periodically modulating an intensity of the interference light from the interference optical system at a predetermined frequency; photo detection means for receiving the interference light whose intensity is modulated by the intensity modulating means to perform photoelectric conversion, storing a charge for only a predetermined storage time, and outputting an electrical signal corresponding to an amount of charge stored; control means for changing the storage time of the photo detection means; and calculation means for calculating a phase and an intensity of the interference light at a depth of the object to be measured, which is detected by the photo detection means based on the electrical signal outputted from the photo detection means every storage time changed by the control means.

Further, according to a second aspect of the present invention, the optical image measuring apparatus according to the first aspect further includes drive means for moving the reference object to scan the object to be measured in a depth direction, wherein the photo detection means successively outputs a plurality of electrical signals based on the interference light, corresponding to a plurality of depths of the object to be measured in scanning caused by the drive means every storage time changed by the control means, and the calculation means calculates a phase and an intensity of the interference light at each of the plurality of depths of the object to be measured, which is detected by the photo detection means based on each of the plurality of electrical signals successively outputted from the photo detection means.

Further, according to a third aspect of the present invention, in the optical image measuring apparatus according to the second aspect, the control means changes the storage time of the photo detection means to change a scanning interval of the scanning caused by the drive means.

Further, according to a fourth aspect of the present invention, the optical image measuring apparatus according to any one of the first to third aspects further includes setting operation means for outputting set value information of the storage time of the photo detection means in accordance with operation of an operator, in which the control means changes the storage time of the photo detection means based on the set value information of the storage time from the setting operation means.

Further, according to a fifth aspect of the present invention, the optical image measuring apparatus according to the second or third aspect further includes setting operation means for outputting set value information of the scanning interval in accordance with operation of an operator, wherein the control means changes the storage time of the photo detection means to a storage time corresponding to the set value information of the scanning interval from the setting operation means.

Further, according to a sixth aspect of the present invention, in the optical image measuring apparatus according to any one of the first to fifth aspects, the photo detection means comprises a CCD camera.

According to the optical image measuring apparatus of the present invention, the storage time of the photo detection means can be changed and the interference light is detected every changed storage time. Therefore, it is possible to obtain the image of the object to be measured at each depth corresponding to the scanning interval according to the storage time. Thus, the scanning interval of the object to be measured in the depth direction thereof can be changed by changing only the storage time. In addition, the scanning interval is changed by charging the storage time of the photo detection means. Therefore, the scanning interval can be changed with high precision.

BRIEF DESCRIPTION OF THE DRAWINGS

In the accompanying drawings:

FIG. 3A to FIG. 3C are diagrams showing an example of an interference light sampling mode of the optical image measuring apparatus according to the embodiment of the present invention, in which FIG. 3A is a graph showing a time waveform of interference light, FIG. 3B is a graph showing an example of a waveform of a sampling function, and FIG. 3C is a graph showing a waveform of sampled interference light;

DETAILED DESCRIPTION OF THE EMBODIMENT

Hereinafter, an example of an optical image measuring apparatus according to an embodiment of the present invention will be described in detail with reference to the accompanying drawings.

Hereinafter, an optical image measuring apparatus having a structure for obtaining a signal intensity of interference light and a spatial phase distribution thereof based on heterodyne signals obtained by receiving interference light beams on three optical paths into which an optical path of the interference light is divided will be described as an embodiment of the present invention. Note that it is possible to suitably employ a structure in which the optical path of the interference light is not divided for detection, a structure in which the optical path of the interference light is divided into two for detection, or a structure in which the optical path of the interference light is divided into four or more for detection.

(Structure of Apparatus)

Figure 1:
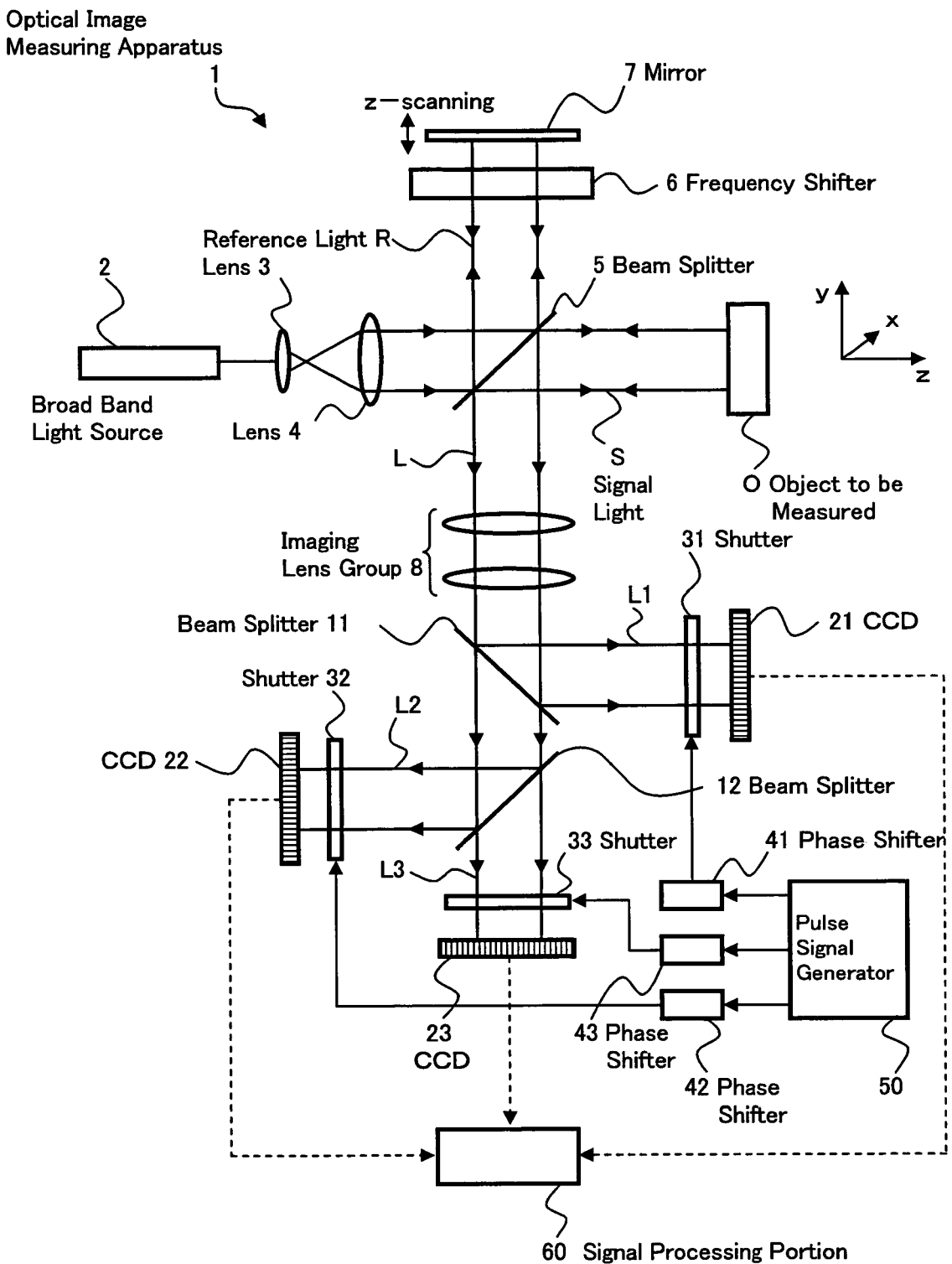
FIG. 1 is a schematic diagram showing an example of an optical image measuring apparatus according to an embodiment of the present invention.

FIG. 1 shows an example of a schematic structure of an optical image measuring apparatus 1 according to the present invention. The optical image measuring apparatus 1 is an apparatus available for, for example, medical use and industrial use and has a structure for obtaining two-dimensional sectional images of an object to be measured O which is made of a scattering medium at respective depths (in z-direction) to form a three-dimensional image.

As in the conventional apparatus, the optical image measuring apparatus 1 includes a broad band light source 2, lenses 3 and 4, a beam splitter 5, and a mirror 7. The light source 2 is composed of an SLD, a light emitting diode (LED), or the like and outputs a low-coherent continuous light beam. The lenses 3 and 4 convert the light beam from the light source 2 into a parallel light flux and widen a beam diameter thereof. The beam splitter 5 divides the light beam into signal light S and reference light R and superimposes the signal light S and the reference light R on each other to produce interference light L. The mirror 7 is a total reflection mirror. Note that a coherent length of an available near-infrared region SLD is about 30 μm and a coherent length of an LED is about 10 μm. Although not shown, a reference mirror driving means for moving the mirror 7 in a propagating direction of the reference light (z-scanning) is provided. The reference mirror driving means will be described later with reference to FIG. 2.

A frequency shifter 6 composed of an optoelectronic modulator, an acoustooptic modulator, or the like is disposed immediately in front of the mirror 7 and shifts a frequency of the reference light R passing therethrough. When a structure is employed in which the reference light R is subjected to Doppler frequency shift by moving the mirror 7, the frequency shifter 6 is unnecessary. However, for example, when it is necessary to increase a shift amount of the frequency (that is, beat frequency) of the reference light R, the apparatus may be constructed such that both the frequency shift caused by the frequency shifter 6 and the frequency shift caused by moving the mirror 7 can be used.

The lenses 3 and 4, the beam splitter 5, the frequency shifter 6, and the mirror 7 compose an "interference optical system" in the present invention. The mirror 7 composes a "reference object" in the present invention.

The optical image measuring apparatus 1 further includes an imaging lens group 8, beam splitters 11 and 12, CCDs (cameras) 21, 22, and 23, and shutters 31, 32, and 33. The imaging lens group 8 images the interference light L produced by the beam splitter 5. The beam splitters 11 and 12 divide the interference light L into three interference light beams L1, L2, and L3. Each of the CCDs 21, 22, and 23 is a storage type two-dimensional photo sensor array for interference light beam detection. The shutters 31, 32, and 33 are disposed immediately in front of the CCDs (camera) 21, 22, and 23, respectively and periodically cut off the interference light beams L1, L2, and L3, respectively. Each of the shutters 31, 32, and 33 is, for example, a high-speed shutter such as a liquid crystal shutter.

The shutters 31, 32, and 33 are not necessarily disposed immediately in front of the CCDs 21, 22, and 23, respectively. The shutters 31, 32, and 33 can be respectively disposed at arbitrary positions on respective optical paths joining branch points of the interference light beams L1, L2, and L3 separated by the beam splitters 11 and 12 with the CCDs 21, 22, and 23. That is, the shutters 31, 32, and 33 may be disposed at positions in which the respective interference light beams L1, L2, and L3 can be cut off to change the quantities of light beams received by the CCDs 21, 22, and 23 to 0.

The CCDs 21, 22, and 23 compose a "photo detection means" in the present invention. The shutters 31, 32, and 33 compose an "intensity modulating means" in the present invention.

The optical image measuring apparatus 1 further includes a pulse signal generator 50 and phase shifters 41, 42, and 43. The pulse signal generator 50 periodically generates a pulse signal. The phase shifters 41, 42, and 43 each shift a phase of the pulse signal generated by the pulse signal generator 50 to produce timing signals for separately controlling open-and-close timings of the respective shutters 31, 32, and 33.

The respective shutters 31, 32, and 33 periodically cut off the interference light beams L1, L2, and L3 at predetermined frequencies, respectively, in response to the timing signals from the phase shifters 41, 42, and 43 in order to sample the respective interference light beams. Therefore, the respective CCDs 21, 22, and 23 periodically receive the corresponding interference light beams L1, L2, and L3. As shown in FIG. 3C later, each of the interference light beams is received as a periodic pulse train. At this time, the respective shutters 31, 32, and 33 are separately opened and closed, with the result that the pulses of the interference light beams L1, L2, and L3 detected by the CCDs 21, 22, and 23 have predetermined phase differences. The CCDs 21, 22, and 23 perform photoelectric conversion on the interference light beams L1, L2, and L3 which are detected at each pixel and output heterodyne signals which are results obtained by the conversion to a signal processing portion 60. The heterodyne signal is an electrical signal reflecting the intensity and phase of the detected interference light beam.

The signal processing portion 60 is a "calculation means" in the present invention, which executes calculation processing described later based on the heterodyne signals outputted from the CCDs 21, 22, and 23. The signal processing portion 60 also analyzes the calculation result to form various images including a two-dimensional sectional image of the object to be measured O and causes a display device such as a monitor device which is not shown to display the images. The signal processing portion 60 is composed of, for example, a computer which includes a storage device such as a ROM storing a predetermined calculation program and a CPU executing the calculation program.

A beam diameter of a light beam emitted from the light source 2 is widened by the lenses 3 and 4. The light beam is divided into the signal light S and the reference light R by the beam splitter 5. The signal light S is incident on the object to be measured O and then incident on the beam splitter 5 again as a reflection light wave including information related to a surface form and inner form of the object to be measured O.

On the other hand, the reference light R passes through the frequency shifter 6 to be subjected to frequency shift, and then propagates to the mirror 7 and is reflected thereon. The reflected reference light R passes through the frequency shifter 6 again to be subjected to additional frequency shift and is incident on the beam splitter 5 again. As described above, the frequency of the reference light R may be shifted by z-scanning of the mirror 7.

A part of the signal light S from the object to be measured O is reflected on the beam splitter 5. Simultaneously, a part of the reference light R subjected to the frequency shift is transmitted through the beam splitter 5. Therefore, the signal light S and the reference light R are superimposed on each other by the beam splitter 5, thereby producing the interference light L. The interference light L passes through the imaging lens group 8 and propagates to the beam splitter 11.

An optical path of the interference light L is divided into two by the beam splitter 11. The interference light beam L1 reflected on the beam splitter 11 is detected by the CCD 21 through the shutter 31.

The optical path of interference light transmitted through the beam splitter 11 is further divided into two by the beam splitter 12. The interference light beam L2 reflected on the beam splitter 12 is detected by the CCD 22 through the shutter 32.

On the other hand, the interference light beam L3 transmitted through the beam splitter 12 is detected by the CCD 23 through the shutter 33.

It is desirable that an interference light dividing ratio of the beam splitter 11, that is, an intensity ratio between the transmitted interference light and the reflected interference light beam L1 be 2:1. In other words, it is desirable that the beam splitter 11 transmit ⅔ of the incident light and reflect ⅓ thereof. In addition, it is desirable that an intensity ratio between the interference light beam L3 transmitted through the beam splitter 12 and the interference light beam L2 reflected thereon be 1:1. In other words, it is desirable that the beam splitter 12 transmit ½ of the incident light and reflect ½ thereof. Therefore, intensity levels of the interference light beams L1, L2, and L3 detected by the CCDs 21, 22, and 23 are made equal to one another. This is suitable to perform calculation processing described later. An intensity ratio between the divided interference light beams is not limited to those and thus can be set as appropriate.

(Structure of Control System)

Figure 2:
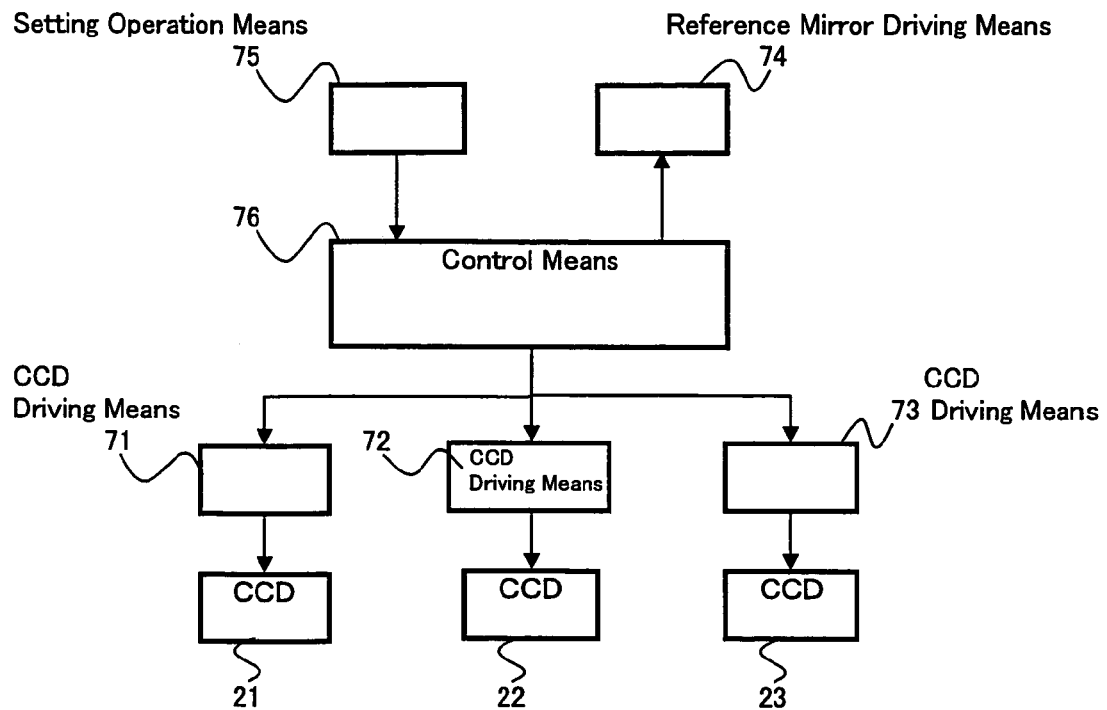
FIG. 2 is a schematic block diagram showing an example of a control system of the optical image measuring apparatus according to the embodiment of the present invention.

Next, a control system of the optical image measuring apparatus 1 according to this embodiment will be described with further reference to a block diagram of FIG. 2. The control system of the optical image measuring apparatus 1 includes CCD driving means 7.1, 72, and 73, a reference mirror driving means 74, a setting operation means 75, and a control means 76. The CCD driving means 71, 72, and 73 respectively control to drive the CCDs 21, 22, and 23. The reference mirror driving means 74 causes the mirror 7 serving as the reference object to move. The setting operation means 75 outputs set value information of a (charge) storage time of the CCDs 21, 22, and 23 in accordance with operation of an operator. The control means 76 controls various operations related to a change in storage time of the CCD 21 and the like.

Each of the CCD driving means 71, 72, and 73 is composed of a CCD driving circuit that generates a pulse signal for controlling the storage time based on a control signal from the control means 76 and outputs the pulse signal to corresponding one of the CCDs 21, 22, and 23.

The reference mirror driving means 74 is composed of a drive device for moving the mirror 7 in the propagating direction of the reference light R (vertical direction in FIG. 1). A drive device having a mechanical structure or an electromagnetic structure can be used as the reference mirror driving means 74 as appropriate. For example, it is possible to use a device including a stepping motor and gears, a solenoid, and the like. The reference mirror driving means 74 composes a "drive means" in the present invention.

The setting operation means 75 is composed of, for example, a keyboard or a mouse in the computer composing the signal processing portion 60. When the storage time of the CCD is set, a predetermined setting screen is displayed on the monitor device of the computer. An operator performs operation based on the predetermined setting screen. When a specific operation panel is provided in the optical image measuring apparatus 1, the setting operation means 75 is provided on the specific operation panel. A touch panel, a keypad, or the like is used as the operation panel. When the setting operation means 75 is operated by the operator in order to set the storage time, the set value information is transmitted as an electrical signal to the control means 76.

The control means 76 is composed of, for example, a CPU of the computer. A control program for controlling the operation of the optical image measuring apparatus 1 based on the set storage time is stored in a memory device of the computer, such as a ROM or a hard disk. The CPU serving as the control means 76 develops the control program on a RAM and generates signals for operation control to output the signals to respective parts of the apparatus.

A subject which is to be actually set using the setting operation means 75 by the operator may be, for example, the scanning interval of the object to be measured O in the depth direction thereof (interval (μm) in the case where scanning is performed in the depth direction) instead of the storage time of the CCD. That is, because what the operator wants to set at the measurement time is the scanning interval, the operability of the apparatus is improved by using a structure for setting the scanning interval. When the structure in which the scanning interval is set by the setting operation means 75 is employed, for example, the following two methods can be applied. According to a first method, the setting operation means 75 calculates a storage time value corresponding to a set value of the scanning interval and transmits the storage time value as an electrical signal to the control means 76. According to a second method, the setting operation means 75 transmits a set value of the scanning interval as an electrical signal to the control means 76. The control means 76 calculates a storage time value corresponding to the electrical signal.

(Measurement Mode)

Subsequently, a measurement mode with respect to the intensity and the phase of the interference light L which are obtained by the optical image measuring apparatus 1 will be described. In the optical image measuring apparatus 1, the interference light beams L1, L2, and L3 for which predetermined phase differences are provided according to the open-and-close timings of the shutters 31, 32, and 33 are sampled for detection. Therefore, the signal intensity of the interference light L and the spatial phase distribution thereof are obtained.

First, when the operator operates the setting operation means 75 to set the storage time of the CCD to a desired value, the setting operation means 75 transmits set value information thereof to the control means 76. The control means 76 controls the CCD driving means 71, 72, and 73 and the reference mirror driving means 74 based on the set value information of the storage time.

A control mode performed by the control means 76 will be specifically described. First, the control means 76 transmits to each of the CCD driving means 71, 72, and 73 a storage time control signal for outputting the pulse signal therefrom every storage time indicated by the set value information. In addition, the control means 76 transmits a reference mirror control signal for controlling the moving speed of the mirror 7 to the reference mirror driving means 74. When the moving speed of the mirror 7 driven by the reference mirror driving means 74 is fixed, it is unnecessary to output the reference mirror control signal from the control means 76.

Each of the CCD driving means 71, 72, and 73 generates the pulse signal every storage time set based on the storage time control signal from the control mean 76 and outputs the generated pulse signal to corresponding one of the CCDs 21, 22, and 23. The storage time of each of the CCDs 21, 22, and 23 is changed and adjusted based on the pulse signal.

The reference mirror driving means 74 is set so as to drive the mirror 7 at a predetermined speed based on the reference mirror control signal from the control means 76. Note that a moving start position of the mirror 7 and a moving direction thereof are separately set according to a depth at which the object to be measured O is scanned. For example, the moving start position is set to a position on the surface of the object to be measured O on the beam splitter 5 side. The moving direction of the mirror 7 is set to a direction from the position on the surface of the object to be measured O to an inner portion thereof.

When the measurement starts, the CCDs 21, 22, and 23 receive the interference light beams L1, L2, and L3 sampled by the shutters 31, 32, and 33 to perform photoelectric conversion. Each of the CCDs 21, 22, and 23 stores a charge for only the set storage time and then outputs an electrical signal corresponding to the amount of charge to the signal processing portion 60. The reference mirror driving means 74 drives the mirror 7 at a predetermined speed to scan the object to be measured O in the depth direction in parallel with the operations of the shutters 31, 32, 33 and the CCDs 21, 22, and 23. Therefore, the object to be measured O is scanned at each desired depth corresponding to the set storage time, with the result that a sectional image at each depth is formed by calculation processing as described later. In particular, even when the reference mirror driving means 74 drives the mirror 7 at a constant speed, it is possible to obtain an image of the object to be measured O at each desired depth.

Such image forming processing will be more specifically described. First, assume that the drive speed of the mirror 7 driven by the reference mirror driving means 74 is a constant value v. In addition, assume that a target image obtaining interval of the object to be measured O in the depth direction is given by d and coordinates of an obtained image in the depth direction are given by D1 (surface on the beam splitter 5 side), D2, D3, . . . At this time, Dn<D(n+1) (n=1, 2, 3, . . . ) and |Dn−D(n+1)|=d. The operator operates the setting operation means 75 to set a target storage time of the CCDs 21, 22, and 23, corresponding to the image obtaining interval d. It is assumed that a set value of the storage time is given by t. As described above, in the case of the structure capable of setting the image obtaining interval using the setting operation means 75, the operator inputs the image obtaining interval d. Here, the storage time of the CCDs 21, 22, and 23 and the image obtaining time are associated with each other by "(image obtaining interval d)=(moving distance of the mirror 7 for the storage time)=(drive speed v of the mirror 7)×(storage time t)". Note that the image obtaining interval is equal to an interval at which the object to be measured O is scanned in the depth direction by driving the reference object (mirror 7) (that is, the above-mentioned scanning interval).

When the operator inputs the set value t of the storage time of the CCDs 21, 22, and 23, the setting operation means 75 transmits the set value t as the set value information to the control means 76. The control means 76 transmits to each of the CCD driving means 71, 72, and 73 the storage time control signal for outputting the pulse signal therefrom every storage time t indicated by the set value information.

The mirror 7 is located at an initial position with the same distance as that of the surface D1 from the beam splitter 5. Upon starting of measurement, the light source 2 outputs a light beam. The CCD driving means 71, 72, and 73 respectively output the pulse signals to the CCDs 21, 22, and 23 at intervals of a period t to set the storage time of the CCDs 21, 22, and 23 to the period t. The reference mirror driving means 74 drives the mirror 7 at the constant drive speed v.

At the time of starting of measurement, the mirror 7 is located at the initial position. Therefore, the CCDs 21, 22, and 23 respectively receive the interference light beams L1, L2, and L3 including reflection light on the surface D1 of the object to be measured O as a coherent component. The CCDs 21, 22, and 23 receive the interference light beams L1, L2, and L3, respectively, and store charges until the pulse signals are inputted from the CCD driving means 71, 72, and 73, that is, during the period t. When the pulse signals are received, each of the CCDs 21, 22, and 23 outputs the electrical signal corresponding to the amount of stored charge to the signal processing portion 60.

During the period t, the mirror 7 is moved by a distance d by the reference mirror driving means 74. Therefore, after the lapse of the period t, the CCDs 21, 22, and 23 respectively receive the interference light beams L1, L2, and L3 including reflection light at the depth D1 of the object to be measured O as a coherent component. The CCDs 21, 22, and 23 receive the interference light beams L1, L2, and L3, respectively, and store charges until an additional period t is elapsed, that is, until a period 2t is elapsed from the time of staring of measurement. In response to next pulse signals from the CCD driving means 71, 72, and 73, each of the CCDs 21, 22, and 23 outputs to the signal processing portion 60 an electrical signal corresponding to the amount of charge stored during the period t from time t to time 2t after the time of starting of measurement.

During the period t from time t to time 2t after the time of starting of measurement, the mirror 7 is further moved by the distance d. Then, the interference light beams L1, L2, and L3 including reflection light at the depth D3 of the object to be measured O as a coherent component are incident on the CCDs 21, 22, and 23, respectively.

As described above, the CCDs 21, 22, and 23 respectively detect the interference light beams L1, L2, and L3 every (storage) time t. A coherent component of each of the interference light beams L1, L2, and L3 detected at each elapsed time k×t (k=1, 2, 3, . . . ) from the time of starting of measurement becomes reflection light of the signal light S at a depth Dk of the object to be measured O. Therefore, the CCDs 21, 22, and 23 successively detect the interference light beams L1, L2, and L3 including coherent components at each of the depths D1, D2, D3, . . . of the object to be measured O every storage time t. Then, results successively obtained by such detection are subjected to the calculation processing described later to calculate the intensities and phases of the interference light beams L1, L2, and L3 corresponding to the plurality of depths D1, D2, D3, . . . of the object to be measured O. Sectional images at the respective depths D1, D2, D3, . . . are formed based on reflectances at the respective depths D1, D2, D3, ... which are acquired from results obtained by the calculation processing.

(Sampling Operation)

Hereinafter, a specific example of interference light sampling operation performed by the optical image measuring apparatus 1 will be described. FIG. 3A to FIG. 3C are explanatory diagrams showing sampling operation of the interference light beam L1 which is performed by the shutter 31. FIG. 3A shows a time waveform of the interference light beam L1 received by the CCD 21 serving as a photo sensor. As expressed by the expression (1), a heterodyne signal related to the interference light beam L1 can be expected to be a signal in which a direct current component composed of background light proportional to the intensity of the reference light R and the intensity of the signal light S is superimposed on an alternating current component having a beat frequency of the interference light beam L1 (which is called a beat signal or the like).

Therefore, the interference light beam L1 is sampled by periodically opening and closing (switching on and off) the shutter 31 based on a sampling function $m_1(t)$ shown in FIG. 3B. The sampling function $m_1(t)$ has a waveform composed of, for example, a rectangular train with a duty of 50% and its frequency $f_{sm}$ is set to a value equal to the beat frequency $f_{if}$ indicated in the expression (1) or close to the beat frequency (that is, $f_{sm}=f_{if}$ or $f_{sm} \approx f_{if}$).

FIG. 3C schematically shows a time waveform of the interference light beam L1 which is allowed to enter the CCD 21 when the interference light beam L1 is sampled using the sampling function $m_1(t)$. A difference between the frequency $f_{sm}$ of the sampling function $m_1(t)$ and the beat frequency $f_{if}$ of the heterodyne signal which is indicated in the expression (1) ($\delta f = |f_{if} - f_{sm}|$) is set to a value sufficiently smaller than a response frequency of the CCD 21 serving as the storage type photo sensor. Therefore, a part of the interference light beam L1 having substantially the same phase is sampled during each period thereof. At this time, an output $i_1(t)$ from the CCD 21 that receives the interference light beam L1 is proportional to the amount of photocharge stored in the CCD 21 during a measurement period. More specifically, the output $i_1(t)$ is expressed by the following expression (for example, see M. Akiba, K. P. Chan, and T. Tanno, Optics Letters, Vol. 28, 816 (2003)).

Expression (2)

$$i_1(t) = \langle K_1 i(t) m_1(t) \rangle \qquad (2)$$

$$= K_1 \left[ \frac{1}{2} I_s + \frac{1}{2} I_r + \frac{2}{\pi} \sqrt{I_s I_r} \cos(2\pi \delta f t + \phi) \right]$$

Here, <-> indicates a time average produced by a storage effect of the CCD 21. In addition, $\phi$ indicates an initial phase value for measurement and $K_1$ indicates photo detection efficiency including reflectance of the beam splitter 11 and a photoelectric conversion rate of the CCD 21.

Similarly, the interference light beam L2 is sampled by the shutter 32 whose open-and-close timings are controlled based on a predetermined sampling function $m_2(t)$ and then detected by the CCD 22. The sampling function $m_2(t)$ has a waveform of a rectangular train with a duty of 50% and a frequency $f_{sm}$ thereof is equal to that of the sampling function $m_1(t)$ for sampling the interference light beam L1. The sampling function $m_2(t)$ has a phase difference $\Delta \theta_{1,2}$ with the sampling function $m_1(t)$. The phase difference $\Delta \theta_{1,2}$ is provided by setting phase shift amounts produced by the phase shifters 41 and 42 in advance. Under the above-mentioned condition, the following output $i_2(t)$ is obtained from the CCD 22 based on the same fundamentals as the expression (2).

Expression (3)

$$i_2 = K_2 \left[ \frac{1}{2} I_s + \frac{1}{2} I_r + \frac{2}{\pi} \sqrt{I_s I_r} \cos(2\pi \delta f t + \phi + \Delta \theta_{1,2}) \right] \qquad (3)$$

Here, $K_2$ indicates photo detection efficiency including transmittance of the beam splitter 11, reflectance of the beam splitter 12, and a photoelectric conversion rate of the CCD 22.

As is apparent from the expressions (2) and (3), each of the outputs from the CCDs 21 and 22 includes the term of an intensity $I_s$ of the signal light S and the term of an intensity $I_r$ of the reference light R. In addition, the output from the CCD 21 includes the term related to an amplitude $\sqrt{(I_s I_r)}$ of the interference light beam L1 and a phase $(2\pi \delta f t + \phi)$ thereof. The output from the CCD 22 includes the term related to an amplitude $\sqrt{(I_s I_r)}$ of the interference light beam L2 and a phase $(2\pi \delta f t + \phi + \Delta \theta_{1,2})$ thereof.

The interference light beam L3 is sampled by the shutter 33 whose open-and-close timings are controlled based on a sampling function $m_3(t)$ and then detected by the CCD 23. The sampling function $m_3(t)$ has a waveform of a rectangular train with a duty of 50% and a frequency $f_{sm}$ thereof is equal to that of the sampling function $m_1(t)$ for sampling the interference light beam L1. The sampling function $m_3(t)$ has a phase difference $\Delta \theta_{1,3}$ with the sampling function $m_1(t)$. The phase difference $\Delta \theta_{1,3}$ is provided by setting phase shift amounts produced by the phase shifters 41 and 43 in advance. At this time, the following output $i_3(t)$ is obtained from the CCD 23 based on the same fundamentals as the expression (2).

Expression (4)

$$i_3 = K_3 \left[ \frac{1}{2} I_s + \frac{1}{2} I_r + \frac{2}{\pi} \sqrt{I_s I_r} \cos(2\pi \delta f t + \phi + \Delta \theta_{1,3}) \right] \qquad (4)$$

Here, $K_3$ indicates photo detection efficiency including respective transmittances of the beam splitters 11 and 12 and a photoelectric conversion rate of the CCD 23.

[Calculation Processing]

Electrical signals outputted from the CCDs 21, 22, and 23 as expressed by the expressions (2), (3), and (4) are transmitted to the signal processing portion 60. The signal processing portion 60 executes the calculation as described below using results outputted from the CCDs 21, 22, and 23. Therefore, the direct current component of the heterodyne signal which corresponds to the background light of the interference light L and is expressed by the expression (1), the signal intensity of the interference light L, that is, the heterodyne signal, and the spatial phase distribution thereof are calculated.

Here, assume that the phase difference $\Delta \theta_{1,2}$ between the sampling function $m_1(t)$ and the sampling function $m_2(t)$ is set to $-\pi/2$ and the phase difference $\Delta \theta_{1,3}$ between the sampling function $m_1(t)$ and the sampling function $m_3(t)$ is set to $\pi/2$. At this time, an intensity $S_1$ of the direction current component of the heterodyne signal which is composed of the background light of the interference light L and phase quadrature components (sine component and cosine component) $S_2$ and $S_3$ thereof are expressed by the following respective expressions.

Expression (5)

$$S_1 = \frac{i_2}{K_2} + \frac{i_3}{K_3} = I_s + I_r \tag{5}$$

Therefore, the intensity of the direct current component corresponding to the background light of the interference light L can be calculated based on the electrical signals from the two CCDs 22 and 23 of the three CCDs 21, 22 and 23.

Expression (6)

$$S_2 = \frac{i_2}{K_2} - \frac{i_3}{K_3} = \frac{4}{\pi}\sqrt{I_s I_r}\sin(2\pi\delta ft + \phi) \tag{6}$$

Expression (7)

$$S_3 = \frac{2i_1}{K_1} - S_1 = \frac{4}{\pi}\sqrt{I_s I_r}\cos(2\pi\delta ft + \phi) \tag{7}$$

When the expressions (6) and (7) are used, the amplitude of the heterodyne signal expressed by the expression (1) is expressed by the following expression.

Expression (8)

$$\sqrt{I_s I_r} \propto \sqrt{S_2^2 + S_3^2} \tag{8}$$

Here, a proportionality factor related to the right side is π/4. The amplitude of the heterodyne signal can be calculated using the direct current component obtained by the expression (5). Therefore, when the direct current component is added to the amplitude of the heterodyne signal, the intensity of the heterodyne signal, that is, the intensity of the reference light L can be obtained.

This indicates that the optical image measuring apparatus 1 is effective for image measurement in which the intensity of the background light is hard to measure in advance, such as optical sectional image measurement for a moving object. It is unnecessary to separately measure the intensity of the direct current component composed of the background light, so that a measurement process can be simplified. Thus, measurement trouble is reduced to shorten a measurement time.

According to the optical image measuring apparatus 1, the spatial phase distribution of the interference light L can be obtained for imaging by the following measurement method.

When the interference components $S_2(t_1)$ and $S_3(t_1)$ of the heterodyne signal which are expressed by the expressions (6) and (7) are obtained at a measurement time $t=t_1$, a signal as expressed by the following expression is calculated from a ratio between both the interference components.

Expression (9)

$$S_4 = \frac{S_2(t_1)}{S_3(t_1)} = \tan(2\pi\delta ft_1 + \phi) \tag{9}$$

As is apparent from the expression (9), a signal $S_4$ does not depend on the amplitude of the interference light L and includes only phase information thereof. Therefore, a phase $\phi(x, y, t_1)$ of the heterodyne signal which is outputted from each of pixels of the CCDs 21, 22, and 23, each of which is the two-dimensional photo sensor array, is expressed by the following expression. Here, (x, y) indicate positional coordinates of each of the pixels which are set on each of the CCDs.

Expression (10)

$$\phi(x, y, t_1) = \tan^{-1}\left[\frac{S_2(x, y, t_1)}{S_3(x, y, t_1)}\right] - 2\pi\delta ft_1 \tag{10}$$

It can be assumed that the second term $2\pi\delta ft_1$ of the expression (10) is an instantaneous phase value of an alternating current signal having a frequency δf of zero or substantially zero at the measurement time $t_1$ and kept constant regardless of a position (that is, variables x, y) of a pixel of each of the CCDs 21, 22, and 23. Therefore, when a difference between a phase $\phi(x_1, y_1, t_1)$ of a heterodyne signal detected from a pixel located at coordinates $(x=x_1, y=y_1)$ on each of the CCDs 21, 22, and 23 and a phase of a heterodyne signal detected from each of pixels are obtained, a spatial phase distribution of the heterodyne signal, that is, a spatial phase distribution of the interference light L can be imaged. It is expected that such measurement of the spatial phase distribution of the interference light is effective for image measurement using phase difference values as references, such as high precision measurement on a mirror surface, which is performed by a heterodyne interference method.

When the phase information is used, frequency information of the interference light L can be obtained. That is, the phase difference δf between the frequency $f_{if}$ of the heterodyne signal and the sampling frequency $f_{sm}$ is calculated by the following expression based on phases $\phi(x, y, t_1)$ and $\phi(x, y, t_2)$ obtained by calculation at two measurement times $t=t_1$ and $t=t_2$.

Expression (11)

$$\delta f = \frac{1}{2\pi}\left|\frac{\phi(x, y, t_1) - \phi(x, y, t_2)}{t_1 - t_2}\right| \tag{11}$$

Because the sampling frequency $f_{sm}$ is known, the frequency $f_{if}$ of the heterodyne signal, that is, the frequency of the interference light L can be calculated based on a result calculated from the expression (11). It is expected that such a heterodyne frequency measuring method is effectively usable for Doppler velocity measurement using a heterodyne interference method, such as blood flow measurement on a fundus of an eye to be examined.

(Operation and Effect)

According to the optical image measuring apparatus 1 having the above-mentioned structure, the storage time of the CCDs 21, 22, and 23 can be changed and the interference light beams L1, L2, and L3 can be detected every changed storage time while the object to be measured O is scanned in the depth direction by moving the mirror 7. Therefore, the object to be measured O can be measured at scanning intervals based on the scanning speed (that is, the drive speed of the mirror 7) and the storage time. When the storage time of the CCDs 21, 22, and 23 is changed, it is possible to easily change the scanning interval of the object to be measured O in the depth direction, that is, the image obtaining interval with high precision.

When the operator uses the setting operation means 75, the storage time of the CCDs 21, 22, and 23 can be set to a desired value. The optical image measuring apparatus 1 executes measurement by scanning the object to be measured O in the depth direction based on the set value. Therefore, the operator can set the scanning interval of the object to be measured O to a desired value, with the result that the measurement can be performed at the set scanning intervals with high precision.

Even when the moving speed of the mirror 7 driven by the reference mirror driving means 74 is fixed to a constant value, the scanning interval of the object to be measured O in the depth direction can be changed by changing the storage time of the CCDs 21, 22, and 23. Therefore, it is possible to easily change the scanning interval of the object to be measured O in the depth direction with high precision while the constitution of the reference mirror driving means 74 is simplified.

According to the optical image measuring apparatus 1, when the storage time of the CCDs 21, 22, and 23 is lengthened, the scanning interval in scanning the object to be measured O, that is, the image obtaining interval can be extended. For example, the scanning interval of about 5 μm in normal use can be increased to about 100 μm. Therefore, an image obtained by an image measuring apparatus having such an image obtaining interval, such as an ultrasonic diagnostic apparatus can be compared with an image obtained by the optical image measuring apparatus 1, so that it is convenient to use.

For example, when an image of a patient as the object to be measured O is obtained to diagnose a region of interest, such as an affected part thereof, an image is first obtained using a large scanning interval and a position of the region of interest is checked based on the obtained image. Then, the region of interest and its vicinity are measured at the scanning interval of about 5 μm with high resolution. Therefore, the position of the region of interest can be easily and speedily determined and a detailed image of the region of interest can be easily and speedily obtained.

It is also possible to scan the object to be measured O in the depth direction while the scanning interval is changed. For example, when a surface part of the object to be measured O and its vicinity are measured in detail and a deep part thereof is not necessarily measured in detail, sectional images of the surface part and its vicinity can be obtained at small steps corresponding to small scanning intervals. On the other hand, sectional images of the deep part can be obtained at large steps corresponding to large scanning intervals. Therefore, according to the optical image measuring apparatus 1 in this embodiment, it is possible to realize the above-mentioned preferable use method by variously changing the scanning interval. Note that the optical image measuring apparatus 1 is not limited to applications to the use method and thus can be applied to various other use methods by changing the scanning interval as appropriate.

(Various Modified Examples)

In the optical image measuring apparatus 1 according to this embodiment, each of the shutters 31, 32, and 33 such as the high-speed shutters is used as the intensity modulating means in the present invention. However, the intensity modulating means is not limited to this. For example, a spatial light modulator (SLM) whose transmittance for transmitting the interference light can be periodically changed is provided instead of such a shutter means that completely cuts off the interference light. Therefore, the intensity of the interference light received by a photo detection means such as the CCD can be modulated to sample the interference light. That is, the shutter means changes the intensity of the interference light received by the photo detection means between 0 and 100 (maximal intensity). A structure for periodically changing the intensity of the interference light between, for example, 10 and 80 can be applied as the intensity modulating means in the present invention.

In addition to changing of the modulated intensity of the interference light between the two values, it is possible to employ a method of periodically switching the intensity among at least three values or a method of periodically and successively switching the intensity between two values based on a sampling mode or the like. An interval for intensity modulation may be determined in view of the sensitivity of the CCD, or the like. If the intensity of the interference light can be periodically modulated, any structure may be employed as the intensity modulating means in the present invention. It is also possible to integrally form the intensity modulating means and the photo detection means.

An arbitrary type of beam splitter can be used as each of the beam splitters 5, 11, and 12. When a cube type beam splitter is used, reflection light on a boundary surface with air is likely to be incident on a CCD. Therefore, it is preferable to use a plate type beam splitter, a wedge type beam splitter, or the like.

In the optical image measuring apparatus 1, the optical system in which the optical path of the illumination system in which the lenses 3 and 4 are disposed is separated from the optical path of the detection system in which the imaging lens group 8 and the like are disposed is used to remove the influences of reflected light from the optical elements located on the respective optical paths.

The three separate CCDs 21, 22, and 23 are provided in the optical image measuring apparatus 1. For example, a three-chip CCD camera (unit) such as 3-CCD type color CCD camera may be used and the intensity modulating means may be disposed in front of each of the CCD chips to construct an apparently single CCD camera. Therefore, it is possible to achieve the simplification of an apparatus structure, the inner space saving of the apparatus, and the like.

When a light receiving surface of a single CCD is divided into a plurality of regions and the intensity modulating means is disposed in front of each of the regions, it is also possible to detect the interference light using each of the regions of the CCD as a single CCD. At this time, a single intensity modulating means composed of, for example, a liquid SLM having a size necessary to cover the plurality of regions of the CCD may be disposed and a region of the intensity modulating means corresponding to each of the regions of the CCD may be controlled to detect the interference light. According to such a structure, it is possible to achieve the simplification of an apparatus structure and the inner space saving of the apparatus. In addition, it is unnecessary to perform sampling with synchronous control of a plurality of CCDs. Therefore, a control system can be simplified.

Offset adjustment of a direct current component of a charge stored in the CCD and gain adjustment of an alternating current signal may be suitably performed to improve the contrast of interference fringes produced by the detected interference light.

When a return mirror for two-reflection or a corner cube is applied as the reference object, a moving distance of the reference object at z-scanning can be shortened. Therefore, the inner space saving of the apparatus can be achieved. In addition, it is possible to reduce a load on the reference mirror drive device 74 and the power consumption thereof when the reference object is moved.

In the above-mentioned embodiment, the sampling is performed at the sampling frequency (substantially) equal to the beat frequency. However, the present invention is not limited to such sampling. For example, when a frequency which is an integral multiple of the beat frequency of the interference light beam is applied as the sampling frequency, each of a plurality of phase ranges of the interference light beam can be periodically sampled. According to such a method, the plurality of phase ranges can be sampled for each period of the interference light beam, so that the interference light can be analyzed more precisely. Therefore, it can be expected to improve the measurement precision.

It is also possible to apply a sampling frequency which is an integral submultiple (1/n) of the beat frequency. According to such a method, a predetermined phase range of the interference light beam is sampled every n-period. Therefore, this method can be efficiently used in the case where the intensity changed by the intensity modulating means cannot follow the beat frequency.

(With Respect to Duty Ratio)

Figure 3:
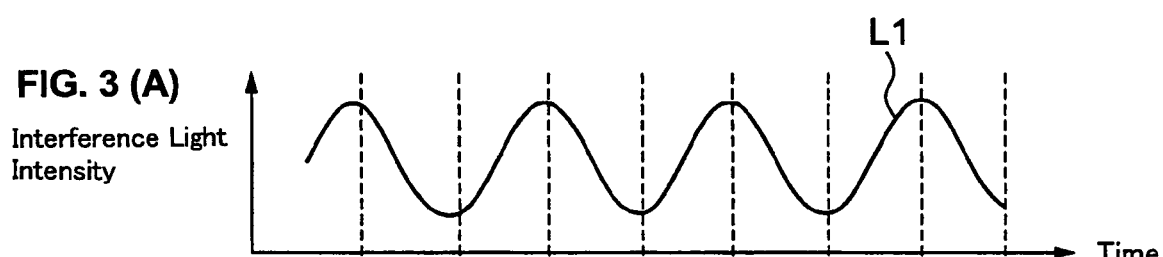
Figure 3:
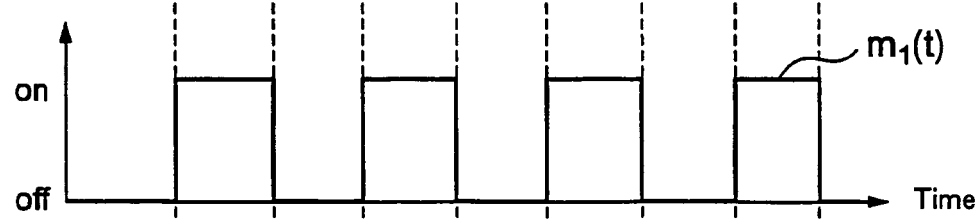
Figure 3:
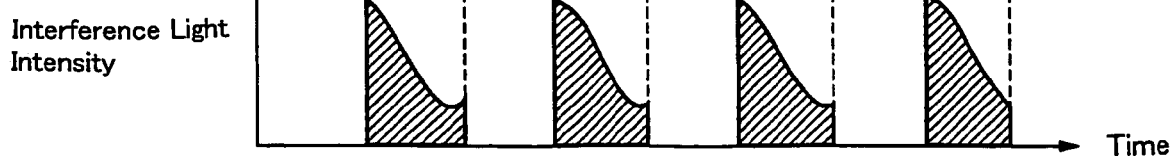
Figure 4:
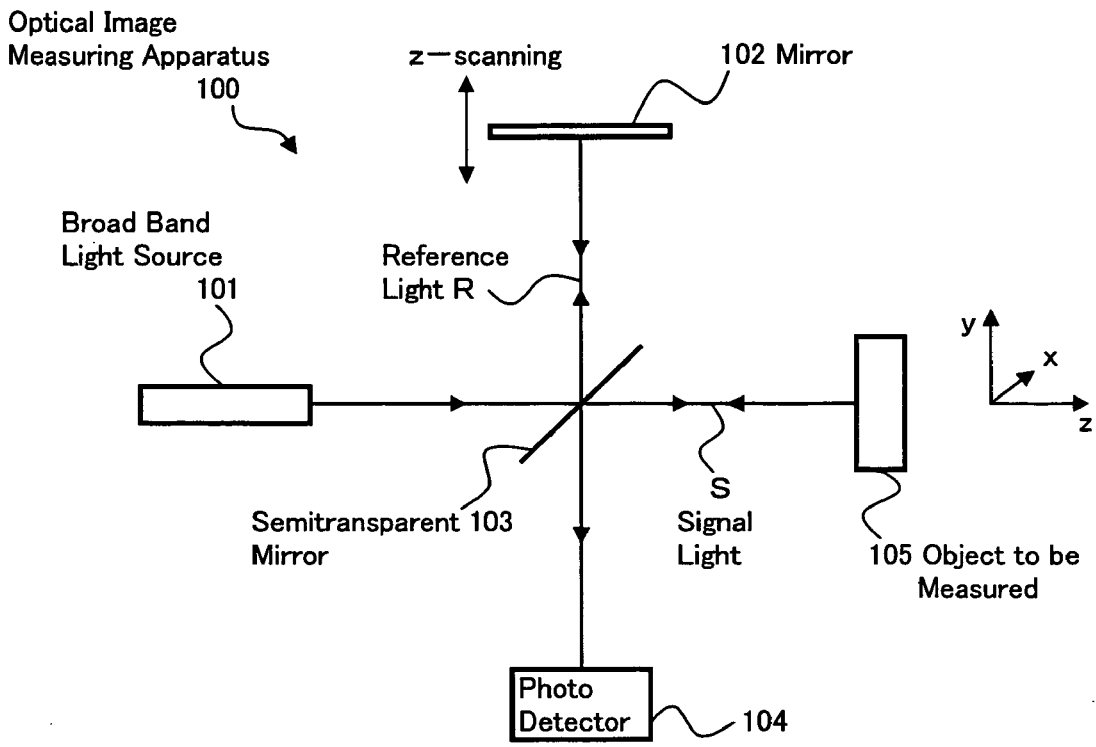
FIG. 4 is a schematic diagram showing a conventional optical image measuring apparatus.
Figure 5:
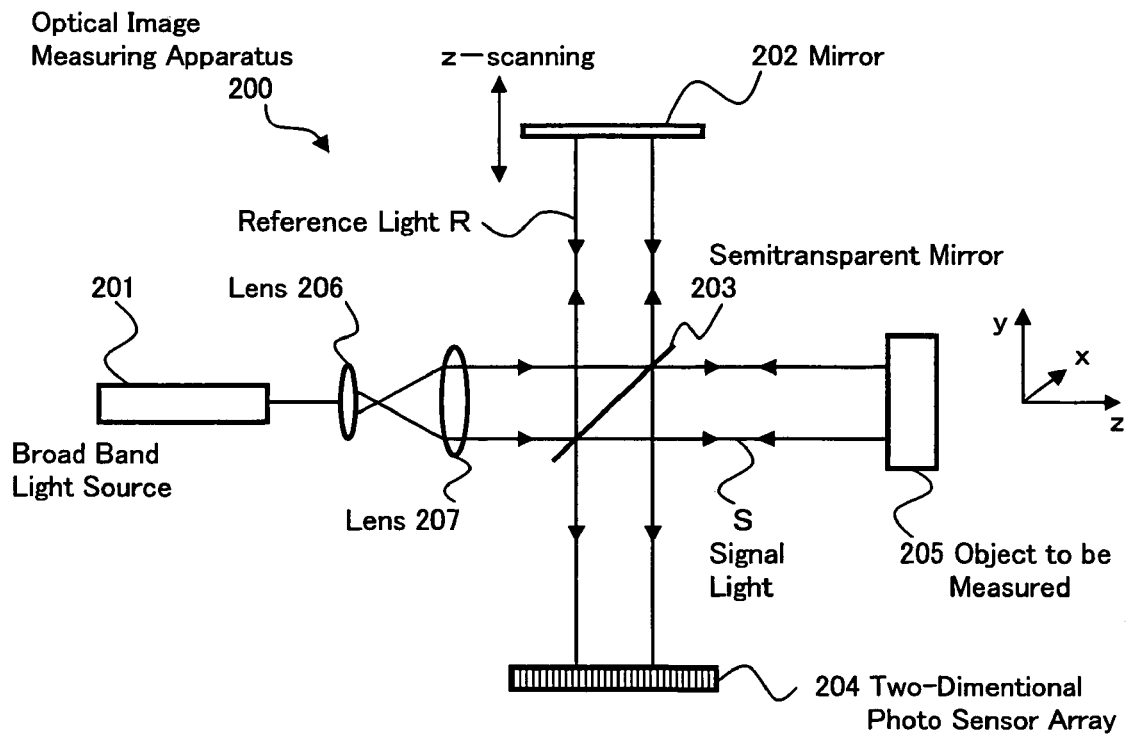
FIG. 5 is a schematic diagram showing a conventional optical image measuring apparatus.

It is preferable that the sampling function used for the optical image measuring apparatus of the present invention have the duty of 50%. This is because when the duty is smaller than 50%, the quantities of light beams received by the CCDs 21, 22, and 23 are decreased to reduce the detection efficiency of the interference light beam. On the other hand, even when the duty ratio exceeds 50%, the detection efficiency reduces. However, for example, when sampling is performed as shown in FIG. 3 to FIG. 5, it is possible to apply a desired duty ratio as appropriate.

With respect to the sampling function used for the optical image measuring apparatus of the present invention, in order to suitably control the open-and-close timings of the shutters 31, 32, and 33, it is preferable to use the rectangular waveform as shown in FIG. 3B. Note that a sampling function having a waveform other than the rectangular wave, such as a sine wave or a triangular wave can be used as appropriate. In particular, when the intensity modulating means other than the shutter means for switching between passing and cutting off of the interference light beam is used, it is possible to effectively use the waveform other than the rectangular wave. For example, when the intensity of the transmitted interference light beam is modulated by successively changing the transmittance of the intensity modulating means using a sampling function having a sine waveform or a triangular waveform, the intensity of the interference light beam received by the CCD can be successively modulated.

When the sampling function having the sine waveform is used, it is expected to improve a calculation speed related to Fourier analysis.

The optical image measuring apparatus according to the present invention is not limited to the structure in which the optical path of the interference light is divided into the three optical paths as in the above-mentioned embodiment. The number of optical paths of the interference light beams is arbitrarily set. When the optical path of the interference light is divided into a plurality of optical paths, it is preferable to use a structure in which the intensity modulating means is provided on each of the optical paths as shown in FIG. 1 or a structure in which the photo detection means such as the CCD is provided on each of the optical paths and the intensity modulating means such as the shutter is provided on each of optical paths other than an optical path. When the latter structure is employed, the interference light beam is successively detected by the photo detection means disposed on an optical path on which the intensity modulating means is not provided and results obtained by detection are time-averaged. Therefore, the direct current component corresponding to the background light of the interference light can be calculated. In addition to such structures, a structure in which the intensity modulating means is provided on at least one of the plurality of optical paths of the interference light beams can be employed as appropriate according to a measurement method and a calculation method.

In addition to the CCDs 21, 22, and 23, for example, a line sensor including an integration circuit can be applied as the photo detection means in the optical image measuring apparatus according to the present invention. Various types of one-dimensional or two-dimensional devices having both a function for receiving the interference light beam and performing photoelectric conversion thereon and a function for storing charges caused by the received interference light beam can be used for the photo detection means in the present invention.

In the embodiment of the present invention as described above, the optical image measuring apparatus having the Michelson type interference optical system is described. It is also possible to use another interference optical system such as a Mach-Zehnder type interference optical system (for example, see JP 3245135 B).

An optical fiber (bundle) used as a light guide member is provided in a part of the interference optical system. Therefore, the degree of freedom of apparatus design can be improved, the apparatus can be made compact, or the degree of freedom of location of the object to be measured can be improved (for example, see JP 3245135 B).

When the optical image measuring apparatus of the present invention is applied to, for example, an ophthalmologic field, two-dimensional sectional images of retina and cornea, and the like can be obtained in addition to the blood flow measurement on the eye fundus. Therefore, it is possible to measure, for example, the number of endothelial cells of the cornea. Various applications are also possible in other fields such as a medical field and an industrial field.

The above-mentioned detailed structures are merely examples of the optical image measuring apparatus according to the embodiment of the present invention. Thus, various modifications can be made without departing from the spirit of the present invention.

What is claimed is:

1. An optical image measuring apparatus for obtaining an image of an object to be measured at a depth corresponding to a position of a reference object based on interference light, comprising:

a light source for emitting a light beam;

an interference optical system that divides the light beam emitted from the light source into signal light propagating through the object to be measured and reference light propagating through the reference object, shifts a frequency of the signal light and a frequency of the reference light relative to each other, and then superimposes the signal light propagating through the object to be measured and the reference light propagating through the reference object on each other to produce the interference light;

intensity modulating means for periodically modulating an intensity of the interference light from the interference optical system at a predetermined frequency;

photo detection means for receiving the interference light whose intensity is modulated by the intensity modulating means to perform photoelectric conversion, storing a charge for only a predetermined storage time, and outputting an electrical signal corresponding to an amount of charge stored;

control means for changing the storage time of the photo detection means; and calculation means for calculating a phase and an intensity of the interference light at a depth of the object to be measured, which is detected by the photo detection means based on the electrical signal outputted from the photo detection means every storage time changed by the control means.

2. An optical image measuring apparatus according to claim 1, further comprising drive means for moving the reference object to scan the object to be measured in a depth direction, wherein the photo detection means successively outputs a plurality of electrical signals based on the interference light, corresponding to a plurality of depths of the object to be measured in scanning caused by the drive means every storage time changed by the control means, and the calculation means calculates a phase and an intensity of the interference light at each of the plurality of depths of the object to be measured, which is detected by the photo detection means based on each of the plurality of electrical signals successively outputted from the photo detection means.

3. An optical image measuring apparatus according to claim 2, wherein the control means changes the storage time of the photo detection means to change a scanning interval of the scanning caused by the drive means.

4. An optical image measuring apparatus according to claim 1, further comprising setting operation means for outputting set value information of the storage time of the photo detection means in accordance with operation of an operator, wherein the control means changes the storage time of the photo detection means based on the set value information of the storage time from the setting operation means.

5. An optical image measuring apparatus according to claim 2, further comprising setting operation means for outputting set value information of the scanning interval in accordance with operation of an operator, wherein the control means changes the storage time of the photo detection means to a storage time corresponding to the set value information of the scanning interval from the setting operation means.

6. An optical image measuring apparatus according to claim 1, wherein the photo detection means comprises a CCD camera.

7. An optical image measuring apparatus according to claim 2, further comprising setting operation means for outputting set value information of the storage time of the photo detection means in accordance with operation of an operator, wherein the control means changes the storage time of the photo detection means based on the set value information of the storage time from the setting operation means.

8. An optical image measuring apparatus according to claim 3, further comprising setting operation means for outputting set value information of the storage time of the photo detection means in accordance with operation of an operator, wherein the control means changes the storage time of the photo detection means based on the set value information of the storage time from the setting operation means.

9. An optical image measuring apparatus according to claim 3, further comprising setting operation means for outputting set value information of the scanning interval in accordance with operation of an operator, wherein the control means changes the storage time of the photo detection means to a storage time corresponding to the set value information of the scanning interval from the setting operation means.

10. An optical image measuring apparatus according to claim 2, wherein the photo detection means comprises a CCD camera.

11. An optical image measuring apparatus according to claim 3, wherein the photo detection means comprises a CCD camera.

12. An optical image measuring apparatus according to claim 4, wherein the photo detection means comprises a CCD camera.

13. An optical image measuring apparatus according to claim 5, wherein the photo detection means comprises a CCD camera.

* * * * *